United States Patent
Klusha et al.

(10) Patent No.: US 7,700,576 B2
(45) Date of Patent: Apr. 20, 2010

(54) PHARMACEUTICAL COMPOSITION ON BASIS OF REVERSE TRANSCRIPTASE INHIBITOR AND MELDONIUM

(75) Inventors: Vija Klusha, Riga (LV); Sergejs Isajevs, Riga (LV); Jolanta Pupure, Riga (LV); Juris Rumaks, Lejasciems (LV); Valentina Gordjushina, Riga (LV); Immanuels Taivans, Riga (LV); Ivars Kalvinsh, Ikshkile (LV)

(73) Assignee: Latvian Institute of Organic Synthesis, Riga (LV)

( * ) Notice: Subject to any disclaimer, the term of this patent is extended or adjusted under 35 U.S.C. 154(b) by 47 days.

(21) Appl. No.: 11/990,285

(22) PCT Filed: Aug. 8, 2006

(86) PCT No.: PCT/LV2006/000005

§ 371 (c)(1),
(2), (4) Date: Feb. 8, 2008

(87) PCT Pub. No.: WO2007/021164

PCT Pub. Date: Feb. 22, 2007

(65) Prior Publication Data

US 2009/0137522 A1    May 28, 2009

(30) Foreign Application Priority Data

Aug. 15, 2005  (LV) .............................. P-05-95

(51) Int. Cl.
*A01N 43/04* (2006.01)
*A61K 31/70* (2006.01)
(52) U.S. Cl. .............................. 514/49; 514/43; 514/45; 514/48; 514/50; 514/51
(58) Field of Classification Search .................. None
See application file for complete search history.

(56) References Cited

OTHER PUBLICATIONS

Sjakste et al. CNS Drug Reviews (2005), vol. 11, pp. 151-168.*
Ferraresi et al. FEBS Letters (2006), vol. 580, pp. 6612-6616.*

* cited by examiner

*Primary Examiner*—Patrick T Lewis
(74) *Attorney, Agent, or Firm*—Colin P. Abrahams

(57) ABSTRACT

Novel pharmaceutical compositions which contain one of the reverse transcriptase inhibitors, viz., Zidovudine, Lamivudine or Stavudine in clinically efficacious amount and Meldonium as well as pharmaceutically applicable excipients. It has been proved that inclusion of Meldonium in these pharmaceutical compositions essentially diminishes the cardio- and neuro-toxicity of the reverse transcriptase inhibitor.

17 Claims, 2 Drawing Sheets

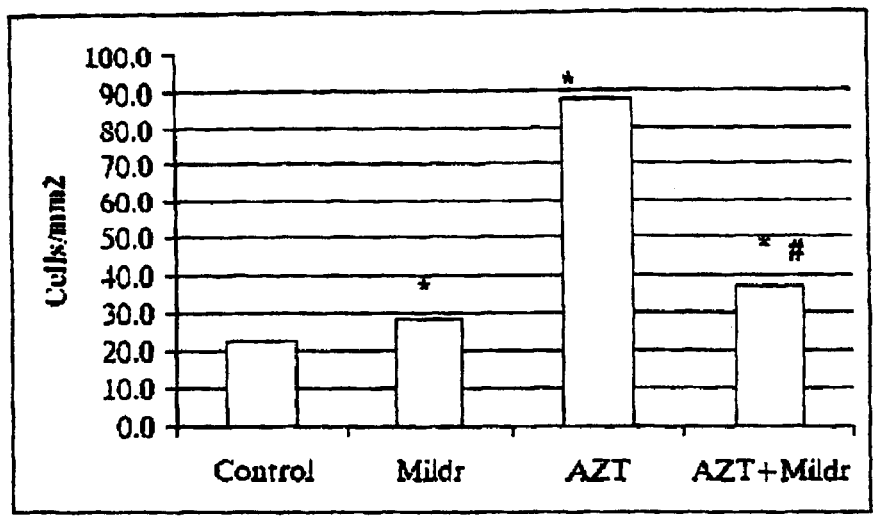
Fig. 1. Total number of NF-kB positive cells in heart tissue.
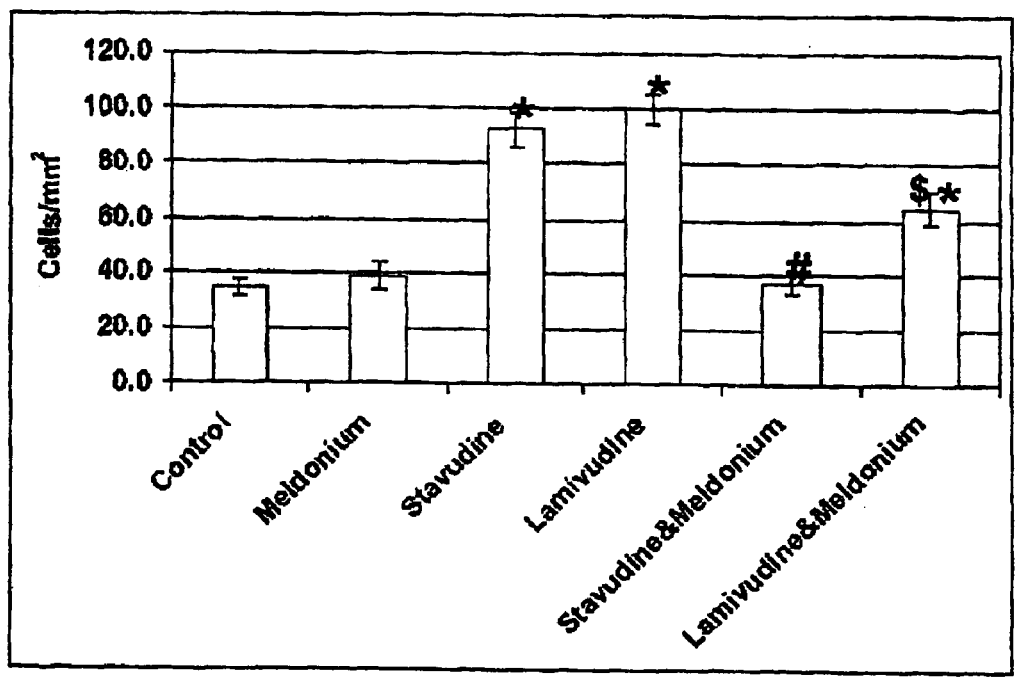
Fig. 2. Total number of NF-kB positive cells in heart tissue.

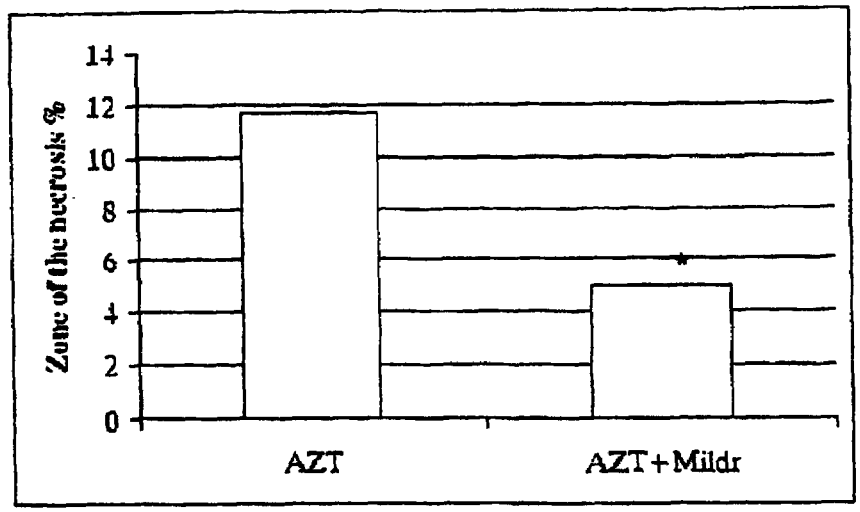
Fig. 3. NF-kB positive cardiomyocytes in the tissue of mice myocardium.
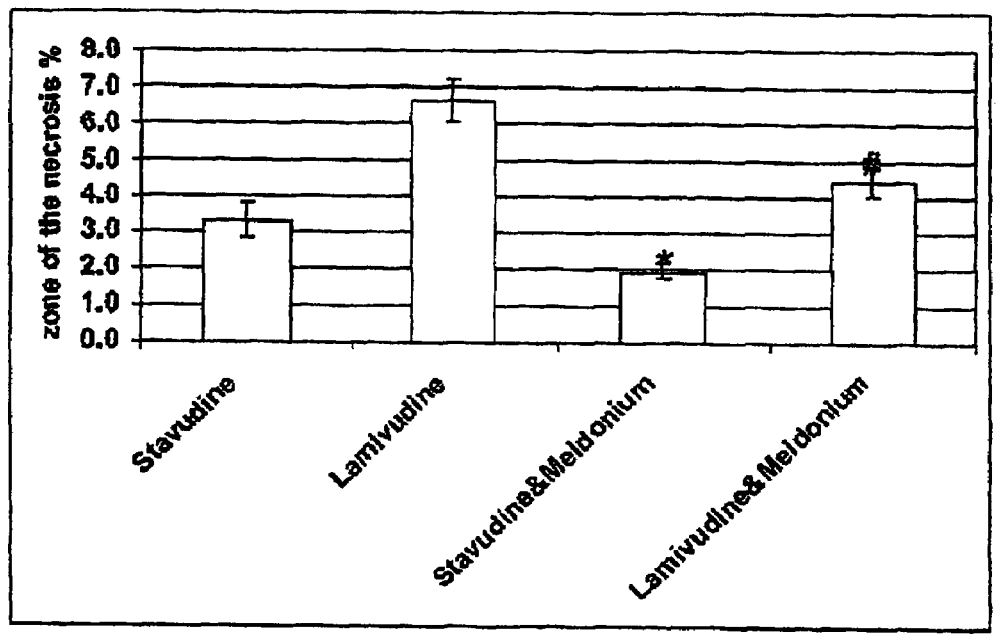
Fig. 4. NF-kB positive cardiomyocytes in the tissue of mice myocardium.

PHARMACEUTICAL COMPOSITION ON BASIS OF REVERSE TRANSCRIPTASE INHIBITOR AND MELDONIUM

TECHNICAL FIELD

This invention relates to a novel therapeutic use of Meldonium and pharmaceutical compositions intended to diminish the toxicity caused reverse transcriptase inhibitor type medicines.

BACKGROUND ART

It is known that the infection of human immunodeficiency virus is one of the most frequent highly dangerous infections having contaged 37.7 million adults and 2.2 million children in late 2004 BROCKLEHURST, P, et al. Antiretrovirals for Reducing the Risk of Mother-to-Child Transmission of HIV Infection. *Cochrane Database Syst Rev.* 2002, no. 2.

In HIV/AIDS treatment, Zidovudine (AZT), Stavudine and Lamivudine that inhibit polymerase-γ, a ferment responsible for HIV-1 mitochondrial deoxyribonucleic acid (mtDNA) replication, are most widely used. Thus, Zidovudine and Stavudine and Lamivudine block the formation of new mitochondria and cause other side effects.

Meldonium, chemically, 3-(2,2,2-Trimethylhydrazinium) propionate is disclosed in U.S. Pat. No. 4,481,218 (INST ORGANICHESKOGO SINTEZA AK (SU)) 8 Jul. 1982.

Meldonium is extensively applied in medicine as an anti-ischemic and stress-protective drug in treating various cardiovascular diseases and other pathologies involving ischemia.

Zidovudine, chemically, 3'-Azido-3'-deoxythymidine; azidothymidine; or AZT is a reverse transcriptase inhibitor. The therapeutic uses of zidovudine and related compounds, and their preparations were disclosed in U.S. Pat. No. 4,724,232 (BURROUGHS WELLCOME CO (US)) 17 Sep. 1985.

Zidovudine is commercially available as 100 mg capsule, 300 mg tablet, 10 mg/mL in 20-mL single-use vial and 50 mg/5 mL in 240 mL syrup.

Lamivudine, chemically, (2R-cis)-4-Amino-1-[2-(hydroxymethyl)-1,3-oxathiolan-5-yl]-2(IH)-pyrimidinone; (−)-2'-deoxy-3'-thiacytidine; (−)-1-[(2R,5S)-2-(hydroxymethyl)-1,3-oxathiolan-5-yl]cytosine; or 3TC is a reverse transcriptase inhibitor. The therapeutic uses of lamivudine and related compounds and their preparations were disclosed in WO 9117159 (IAF BIOCHEM INT (CA)) 2 May 1991

Lamivudine is commercially available as 100 mg, 150 mg and 300 mg tablets; 10 mg/mL in 240 mL oral solution.

Stavudine, chemically, 2',3'-Didehydro-3'-deoxythymidine; 1-(2,3-dideoxy-β-glycero-pent-2-enofuranosyl)thymine; or 3'-deoxy-2'-thymidinene is a reverse transcriptase inhibitor. The therapeutic uses of stavudine and related compounds and their preparations were disclosed in U.S. Pat. No. 5,130,421 (BRISTOL MYERS CO (US)) 29 Apr. 1991

Stavudine is commercially available as 15 mg, 20 mg, 30 mg and 40 mg capsules; and 1 mg/mL in 200 ml oral solution.

Several approaches are known how the adverse reactions caused by Zidovudine, Stavudine and Lamivudine toxicity may be restricted. Nevertheless, none has simultaneous effect on functioning of both cardiomyocytes and neurons.

For the purpose of diminishing mitochondrial damage, additional use of antioxidants, e.g. very high doses of Vitamin C and Vitamin E is recommended in particular cases BROCKLEHURST, P, et al. Antiretrovirals for Reducing the Risk of Mother-to-Child Transmission of HIV Infection. *Cochrane Database Syst Rev.*, 2002, no. 2; FICHTENBAUM, C. J. Coronary Heart Disease Risk, Dyslipidemia, and Management in HIV-Infected Persons. *HIV Clin Trials.* 2004 November-December, vol. 5, no. 6, p. 416-433.

It is proved in trials on mice that daily doses of Vitamin C 1,250 mg/kg and daily doses of Vitamin E 75 mg/kg protect mitochondria against oxydative stress as well as reduce the activity of aspartate aminotransferase (AST) and lactate dehydrogenase (LDH) and also confine the damage of mitochondrial ultrastructure. Creatine kinase (CK) activity similarly subsides which reinforces in case of zidovudine application PETERS, B. S., et al. Mitochondrial Myopathy Associated with Chronic Zidovudine Therapy in AIDS. *Q J Med.* 1993 January, vol. 86, no. 1, p. 5-15.

Coenzyme Q10 may be regarded as another substance capable of exerting a positive influence in preclusion of zidovudine adverse reactions by activating electron transfer in the respiration chain; riboflavin, tocopherol, succinates, ascorbinic acid, Menadione, and nicotinamide putatively inhibit the respiration chain blockage LARSSON, N. G., et al. Mitochondrial Myopathies. *Acta Physiol Scand.* 2001, no. 171, p. 225-233.

WO 9705864 (SIGMA TAU IND FARMACEUTI (IT); MENDES SRL (IT); MORETTI SONIA (IT)) 19 Jul. 1996 provides information concerning a novel use of L-carnitine, the derivatives thereof and their pharmacologically acceptable salts in combination with antiretroviral drugs for reducing ceramide levels, enhancing the activity of the aforesaid antiretroviral drugs for the therapeutic treatment of HIV-infection and AIDS and enhancing the immune system affected by these drugs.

In EP 0560275 A (SIGMA TAU IND FARMACEUTI (IT)) 9 Mar. 1993 were disclosed a novel therapeutic utilization of L-carnitine and the pharmacologically acceptable salts thereof for treating carnitine-depleted HIV-seropositive patients.

DISCLOSURE OF THE INVENTION

Technical Problem

In AIDS treatment, Zidovudine (AZT), Stavudine and Lamivudine, that inhibit polymerase-γ, an enzyme responsible for HIV-1 mitochondrial deoxyribonucleic acid (mtDNA) replication, are most widely used. Thus, Zidovudine and Stavudine and Lamivudine block the formation of new mitochondria.

However, the drug dosage forms and compositions containing AZT, Stavudine and Lamivudine have a major disadvantage consisting in the use restrictions imposed by the adverse effects of AZT, Stavudine and Lamivudine toxicity (LEWIS, W, et al. Zidovudine Induces Molecular, Biochemical, and Ultrastructural Changes in Rat Skeletal Muscle Mitochondria. *Journal of Clin Invest.* 1992 April, vol. 89, no. 4, p. 1354-1210; SZABADOS, E, et al. Role of Reactive Oxygen Species and Poly-ADP-ribose Polymerase in the Development of AZT-induced Cardiomyopathy in Rat. *Free Radic Biol Med.* 1999 February, vol. 14, no. 3-4, p. 189-197; BLANCO, F. First-line Therapy and Mitochondrial Damage: Different Nucleosides, Different Findings. *HIV Clin Trials.* 2003 January-February, vol. 4, no. 1, p. 11-19; BISHOP, J. B, et al. Mitochondrial Damage Revealed by Morphometric and Semiquantitative Analysis of Mouse Pup Cardiomyocytes Following in Utero and Postnatal Exposure to Zidovudine and Lamivudine. *Toxicol Sci.* 2004, vol. 81, no. 2, p. 512-517.

AZT toxicity is largely linked also with its capacity of incorporation into mitochondria (NUSBAUM, N. J. AZT Incorporation into Mitochondria: Study in Human Myeloid Cell Line. *DNA Cell Biol.* 1996, no. 15, p. 363-366.) that causes elimination of mtDNA and cytochrome C (CYC) in them. Diminishing activity of oxydative phosphorylation enzymes is concurrently observed. It induces abatement of the level of adenosine triphosphate (ATP) produced by mitochondria and accumulation of reactive oxygen species (ROS), therefore cell anaerobic respiration intensifies and lactate builds up.

The toxic effects of zidovudine and lamivudine clinically appear as myopathy of muscle cells caused by mitochondrial pathologies which besides arise due to HIV infection itself (PETERS, B. S., et al. Myopathy Associated with Chronic Zidovudine Therapy in AIDS. *Q J Med.* 1993 January, vol. 86, no. 1, p. 5-15; BAKKER, H. D., et al. Vitamin-Responsive Complex-1 Deficiency in a Myopathic Patient with Increased Activity of the Terminal Respiratory Chain and Lactic Acidosis. *J Inherit Metab Dis.* 1994, no. 17, p. 196-204; SULKOWSKI, M. S., et al. Hepatic Steatosis and Antiretroviral Drug Use Among Adults Co-infected with HIV and Hepatitis C Virus. *AIDS.* 2005 Mar. 24, vol. 19, no. 6, p. 585-592; LICHTERFELD, M., et al. Fatty Liver and Increased Serum Lactate in a Woman with HIV. *Dtsch Med Wochenschr.* 2003 Jan. 17, vol. 98, no. 3, p. 81-84; DE LA ASUNCION, J. G., et al. AZT Induces Oxidative Damage to Cardiac Mitochondria: Protective Effect of Vitamins C and E. *Life Sci.* 2004 Nov. 19, vol. 76, no. 1, p. 29-56. BISHOP, J. B., et al. Mitochondrial Damage Revealed by Morphometric and Semiquantitative Analysis of Mouse Pup Cardiomyocytes Following in Utero and Postnatal Exposure to Zidovudine and Lamivudine. *Toxicol Sci.* 2004, vol. 81, no. 2, p. 512-517.

Mitochondrial damage usually primarily affects the functioning of muscle cells since the latter are distinguished by high energy consumption LARSSON, N. G, et al. Mitochondrial Myopathies. *Acta Physiol Scand.* 2001, no. 171, p. 225-233.

It is the cardiac muscle which is most severely affected by myopathies SZABADOS, E., et al. Role of Reactive Oxygen Species and Poly-ADP-ribose Polymerase in the Development of AZT-induced Cardiomyopathy in Rat. *Free Radic Biol Med.* 1999 February, no. 14, p. 3-4 and 189-197; BISHOP, J. B., et al. Mitochondrial Damage Revealed by Morphometric and Semiquantitative Analysis of Mouse Pup Cardiomyocytes Following in Utero and Postnatal Exposure to Zidovudine and Lamivudine. *Toxicol Sci.* 2004, vol. 81, no. 2, p. 512-517; GERSCHENSON, M., et al. Fetal Mitochondrial Heart and Skeletal Muscle Damage in Erythrocebus Patas Monkeys Exposed in Utero to 3'-azido-3'-deoxythymidine. *AIDS Res Hum Retroviruses.* 2000 May 1, vol. 16, no. 7, p. 635-626.

Zidovudine and other nucleoside reverse transcriptase inhibitors (NRTIs) (Lamivudine, and Stavudine) frequently create sensory neuropathy, too, that contributes to deterioration of patients' quality of life (Cherry et al., J Clin Virol 2003, 26:195-207).

Main problem is to find agents that diminish the toxicity caused by the reverse transcriptase inhibitor type medicines. Such agents would enable to use effective doses of the reverse transcriptase inhibitors with lower adverse effects.

Technical Solution

While attempting to make a pharmaceutical composition for retrovirus infection treatment distinguished by essentially lower toxicity, we unexpectedly discovered that doses adequate to the therapeutic ones used in the clinic of pharmaceutical compositions containing Meldonium [3-(2,2,2-trimethyl hydrazinium) propionate dihydrate], a drug for treating cardiac insufficiency, coadministered or used in pharmaceutical composition with Zidovudine, Lamivudine, or Stavudine or some other known clinically applicable reverse transcriptase inhibitor efficiently preclude the damage of myocytes, particularly cardiomyocytes caused by reverse transcriptase inhibitors including Zidovudine, Lamivudine, and Stavudine.

A number of substances had been proposed for reducing the toxicity of reverse transcriptase inhibitors.

Therefore the cardioprotective effect of Meldonium, which is known to lower the lever of carnitine and decrease the activity of carnitine palmitoyltransferase (DAMBROVA, M, et al. Mildronate: Cardioprotective Action through Carnitine-Lowering Effect. *Trends Cardiovasc Med.* 2002, no. 9, p. 155-159.), is unexpected and surprising.

Pharmaceutical compositions containing a reverse transcriptase inhibitor and Carnitine and the use of a reverse transcriptase inhibitor in combination with carnitine are well known in the prior art.

Carnitine and Meldonium are structurally very similar. However, the pharmacolgical effect of Meldonium has been regarded as counteracting the effect of Carnitine. Consequently, it is not considered obvious to the man skilled in the art to combine a reverse transcriptase inhibitor with Meldonium.

The surprising effect of Meldonium can not be explained also by other activity. Because Meldonium is not oxidized in the organism of warm-blooded animals and humans, it cannot be regarded as an antioxidant of direct action that principally differentiates it from reducing vitamins or metabolites so far used for precluding the adverse reactions of zidovudine, lamivudine, and stavudine.

There are no references in the literature that Meldonium as a molecule could participate in electron transport in the chain of mitochondrial respiration. Thereby it essentially differs also from coenzyme Q10, nicotinamide and similar substances possibly having such mechanism of action. Likewise data is lacking that Meldonium has any antiviral properties.

As a result, the capability unexpectedly discovered by us of Meldonium alone or in therapeutical compositions containing reverse transcriptase inhibitors, e.g. zidovudine, lamivudine, and stavudine and Meldonium or its pharmaceutical acceptable salts to essentially suppress the toxic adverse effects caused by these antiviral drugs, in particular cardiomyopathy and neurotoxicity, with no deterioration of their specific antiviral activity has not been previously known, and it essentially differs from known compositions containing reverse transcriptase inhibitors.

It is common knowledge that Meldonium as a pharmacologic active is characterized by extremely low toxicity (more than 25,000 mg/kg, p.o. for mice), it is neither teratogenic, embryotoxic nor carcinogenic and practically exerts no adverse influence on human organism.

We discovered that it is also a chemically sufficiently inert substance which may be combined in formulations even with such complicated and chemically sensitive substances as nucleoside analogues including Zidovudine, Lamivudine, and Stavudine.

We discovered that in the therapeutical composition the ratio of Meldonium to the reverse transcriptase inhibitor may be from 1:100 to 100:1. In experiments with compositions containing, for instance, Zidovudine, Lamivudine or Stavudine and Meldonium we established that ratios of Meldonium to Zidovudine, Lamivudine or Stavudine may vary from 1:5 to 5:1, though ratios from 1:2 to 2:1 are preferable.

Pharmaceutical compositions may be also made on the basis of Meldonium and other reverse transcriptase inhibitors; compositions of Meldonium or its pharmaceutical acceptable salts and Zidovudine, Lamivudine or Stavudine are non-exhaustive examples.

In oral dosage forms, Zidovudine, Lamivudine or Stavudine content is 5-500 mg per tablet, capsule, caplet, or other suitable dosage form.

The therapeutic compositions containing Zidovudine, Lamivudine or Stavudine and Meldonium may be formed for both oral and parenteral introduction. In particular cases, transdermal introduction forms may also be used.

For oral introduction, capsules, tablets, caplets, pills, powders, syrups and other dosage forms containing Zidovudine, Lamivudine or Stavudine and Meldonium and suitable for oral introduction may be used which include pharmaceutically compliant excipients besides Zidovudine, Lamivudine or Stavudine and Meldonium. These therapeutic forms can be prepared by commonly known procedures of oral dosage forms.

The quantity of Zidovudine, Lamivudine or Stavudine and the advised daily dose of the composition of Zidovudine, Lamivudine or Stavudine with Meldonium shall provide pharmaceutically sufficient level of Zidovudine, Lamivudine or Stavudine in human organism, and typically constitutes 1-15 mg/kg for humans, correspondingly 10-150 mg/kg for mice. In cases where the reverse transcriptase inhibitor of the claimed composition is Zidovudine, Lamivudine or Stavudine, tablets, caplets, capsules or other appropriate oral introduction form of Zidovudine, Lamivudine or Stavudine and Meldonium compositions normally shall contain 10 to 300 mg of Zidovudine, Lamivudine or Stavudine and 5-1000 mg of Meldonium. For parenteral introduction, Zidovudine, Lamivudine or Stavudine in concentrations of 10-20 mg/ml and Meldonium in concentrations of 50-400 mg/ml are recommended for this dosage form.

Pharmaceutical compositions may be formed on basis of Meldonium and other reverse transcriptase inhibitors, exemplified but not restricted to Zidovudine, Lamivudine or Stavudine, the reverse transcriptase inhibitor having the same ratio to Meldonium as in pharmaceutical compositions of Zidovudine, Lamivudine or Stavudine and Meldonium or its pharmaceutically acceptable salts.

The essence of the invention is illustrated by but not limited to the following examples.

The cardiotoxic action of Zidovudine and Meldonium pharmaceutical compositions was investigated by introducing them into male mice of initial mass 15.69±1.56 g during a fortnight. Throughout the experiment, the animals were kept in standard laboratory conditions at temperature of 22±0.5° C. and 12 hours light/darkness cycle, being fed with standard laboratory animal food. For the control group (n=6), 10 ml of 0.9% NaCl aqueous solution was intraperitoneally introduced daily (1st and $12^{th}$ group).

In a series of experiments, the following solutions were administered intraperitoneally for animal trial groups (including 6 mice each) daily.

Experimental series no. 1:
1st group—Control,
2nd group—Meldonium 100 mg/kg in 0.9% NaCl solution,
3rd group—Zidovudine 50 mg/kg in 0.9% NaCl solution,
4th group—150 mg/kg pharmaceutical composition consisting of zidovudine and Meldonium 1:2 (by mass) dissolved in 0.9% NaCl aqueous solution,
$5^{th}$ group Meldonium 100 mg/kg in 0.9% NaCl solution and Zidovudine 50 mg/kg in 0.9% NaCl solution, Experiment series no. 2:
6th group—Stavudine 50 mg/kg in 0.9% NaCl solution,
7th group—Lamivudine 50 mg/kg in 0.9% NaCl solution,
8th group—150 mg/kg pharmaceutical composition consisting of Stavudine and Meldonium 1:2 (by mass) dissolved in 0.9% NaCl aqueous solution,
9th group—150 mg/kg pharmaceutical composition consisting of Lamivudine and Meldonium 1:2 (by mass) dissolved in 0.9% NaCl aqueous solution,
10th group—Meldonium 100 mg/kg in 0.9% NaCl solution,
11th group—Meldonium 100 mg/kg in 0.9% NaCl solution and Stavudine 50 mg/kg in 0.9% NaCl solution,
12th group—Meldonium 100 mg/kg in 0.9% NaCl solution and Lamivudine 50 mg/kg in 0.9% NaCl solution,
13th group—control.

On the 15th day of the trial, the animals were decapitated, hearts were taken out and placed into 10% formalin solution. For immuno-histochemical research, organs were fixed in paraffin, and preparations of 4 µm thickness were sliced which were tinged according to the avidin-biotin immuno-histochemical method by use of DAKO LSAB reagent kit. Having deprived the preparations of fat, we fixed them with a reagent blockading peroxidase (hydrogen peroxide and sodium azide 0.015 mol/l) for 10 min, rinsed with an isotonic buffer (pH 7.6) and then incubated in a humidity chamber with rabbit polyclonal NF-kBp65 antibodies (Abcam, Ltd) (1:200) at 4° C. for 12 hours.

We incubated the preparations with biotinylated anti-goat IgG for 30 min at room temperature. Thereafter sections were incubated them with enzyme-labelled Strepavidin. The colour reactions of immunoperoxidase was developed by incubation with diaminobenzidine. At tinging procedures, lung parenchyma (alveolar macrophages) was constantly used as the positive control and tissue without previous treatment with primary antibodies was used as the negative control. The number of NF-kBp65 positive cells (in both cytoplasmatic and nuclear staining) was counted by the blind method. For quantitative assessment, image analysis software Motic Image, Motic, and Image ProPlus, Leica, 4000B was used. All cell counts were expressed as cells per 1 $mm^2$. In the heart, NF-kBp65 positive cardiomyocyte nuclei were counted in high-power fields (×400), and their total number was recorded.

The results were expressed as mean ±SEM. For analysis of statistical reliability we used the unpaired t-test (Mann Whitney U test) at confidence level $P<0.05$.

We discovered that, as compared to control, AZT, Stavudine or Lamivudine induces perivascular oedema, degeneration of myocardium adipose tissue and infiltration with leucocytes what initiate cardiomyocitytes necrosis. Meldonium which was administered together with AZT, Lamivudine or Stavudine and pharmaceutical compositions of Meldonium/AZT, Meldonium/Stavudine or Meldonium/Lamivudine in ratio, e.g. 2:1 significantly decreased perivascular and stromal oedema, prevented cardiomyocyte necrosis, myocardium adipose tissue degeneration and leucocyte infiltration.

FIG. 1 of the drawings appended hereto shows total number of NF-kB positive cells in heart tissue. Captions: Control—the control group, Mildr—Meldonium group, AZT—AZT group, AZT+Mildr— the group of Meldonium/AZT pharmaceutical composition. The statistical reliability is calculated as* $P<0.05$ relative to the control group; #P0.05 to AZT group.

TABLE 1

| | NF-kBp65 positive cells in mouse heart tissue, mm2 | | | |
| --- | --- | --- | --- | --- |
| | Control | Meldonium | AZT | Meldonium&AZT |
| Average | 22.7 | 27.9 | 88.1 | 36.8 |

In FIG. 1 and in Table 1 the results are shown which prove the total (localized in nuclei and cytosol) NF-kBp65 activation induced by AZT which is statistically reliable ($P<0.05$) while the pharmaceutical composition of Meldonium/AZT damages myocardium essentially less what is evidenced by the fact that NF-kB activity is reduced impressively ($P<0.05$) in case of Meldonium/AZT composition as compared to AZT group. The same result was obtained group where Meldonium and AZT were administrated separately. Moreover, when the proposed medical use of Meldonium and Meldonium/AZT compositions were used, NF-kBp65 activity did not significantly differ from the parameters of the intact control group animals.

FIG. 2 of the drawings appended hereto show total number of NF-kB positive cells in heart tissue. Captions: Control—the control group, Meldonium—Meldonium group, Stavudine—Stavudine group, Lamivudine—Laniivudine group, Stavudine & Meldonium—the group of Stavudine/Meldonium pharmaceutical composition, Lamivudine & Meldonium—the group of Lamivudine/Meldoniuni pharmaceutical composition. The statistical reliability is calculated as* P>0.05 relative to the control group; #P>0.05 to Stavudine group; $<0.05 to Lamivudine group.

TABLE 2

NF-kBp65 positive cells in mouse heart tissue, mm2

|  | Control | Meldonium | Stavudine | Lamivudine | Stavudine &Meldonium | Lamivudine &Meldonium |
| --- | --- | --- | --- | --- | --- | --- |
| Average | 34.7 | 38.8 | 92.5 | 100.1 | 36.6 | 64.3 |

In FIG. 2 and in Table 2 the results are shown which prove the total (localized in nuclei and cytosol) NF-kBp65 activation induced by Stavudine and Lamivudine which is statistically reliable (P<0.05) while the pharmaceutical composition of Meldonium/Stavudine or the pharmaceutical composition of Meldonium/Lamivudine damages myocardium significantly less what is evidenced by the fact that NF-kB activity is reduced substantially in case of Meldonium/Stavudine composition or in case of Meldonium/Lamivudine composition as compared to Stavudine and Lamivudine group. The same results were obtained from the groups where Meldonium and Lamivudine or Stavudine were administrated separately. Moreover, when the proposed compositions were used, NF-kBp65 activity did not significantly differ from the parameters of the intact control group animals.

FIG. 3 of the drawings show NF-kB positive cardiomyocytes in the tissue of mice myocardium. The statistical reliability is calculated as * P<0.05 relative to AZT group.

TABLE 3

Zone of the necrosis %

|  | AZT | AZT&Meldonium |
| --- | --- | --- |
| Average | 11.7 | 5 |

The activation of NF-kBp65 localized in cardiomyocyte nuclei (FIG. 3 and tab. 3) was only observed for AZT- and AZT+ Meldonium groups. Namely in this case of the claimed use of Meldonium and AZT pharmaceutical composition, the NF-kB activity level was impressively lower as compared to the parameters of the AZT group (P<0.05). The same result was obtained from the group where Meldonium and AZT were administrated separately.

FIG. 4 of the drawings show NF-kB positive cardiomyocytes in the tissue of mice myocardium. The statistical reliability is calculated as * P<0.05 relative to Stavudine group. The statistical reliability is calculated as #PO0.05 relative to Lamivudine group.

TABLE 4

Zone of the necrosis %

|  | Stavudine | Lamivudine | Stavudine& Meldonium | Lamivudine& Meldonium |
| --- | --- | --- | --- | --- |
| Average | 3.3 | 6.6 | 2.0 | 4.4 |

The activation of NF-kBp65 localized in cardiomyocyte nuclei (FIG. 4 and Tab. 4) was only observed for Stavudine and Lamivudine and Meldonium/Stavudine or Meldonium/Lamivudine pharmaceutical compositions. Namely in this case of the claimed Meldonium/Stavudine and Meldonium/Lamivudine pharmaceutical composition use, the NF-kB activity level was impressively lower as compared to the parameters of the Stavudine and Lamivudine groups (P<0.05). The same result was obtained from the groups where Meldonium and AZT were administrated separately The research has shown that AZT essentially increases both the total number of NF-kBp65 positive cells in heart tissue and that of NF-kBp65 in cardiomyocyte nuclei. On the contrary, the claimed parallel Meldonium and AZT, Stavudine or Lamivudine administration and pharmaceutical composition of Meldonium and AZT, Meldonium and Stavudine or the pharmaceutical composition of Meldonium and Lamivudine essentially diminishes both the total number of NF-kBp65 positive cells in heart tissues and NF-kBp65 in cardiomyocyte nuclei.

Affirmative results were also obtained with other Meldonium/AZT, Meldonium/Stavudine or Meldonium/Lamivudine ratios in the pharmaceutical composition, the minimal adverse effects being established if Meldonium/AZT, Meldonium/Stavudine or Meldonium/Lamivudine ratios were from 5:1 to 1:2.

As Meldonium bioavailability is very high in oral introduction, considerably lower toxic effects of Meldonium/AZT, Meldonium/Stavudine or Meldonium/Lamivudine pharmaceutical compositions than those of AZT, Lamivudine or Stavudine therapeutical forms were established for both parenteral and enteral introduction.

Thus, the results show that co-administration of Meldonium and AZT, Lamivudine or Stavudine and the administration of pharmaceutical compositions containing Meldonium/AZT, Meldonium/Stavudine or Meldonium/Lamivudine are essentially different from AZT, Lamivudine or Stavudine as to the toxic effect on myocardium and neurons. AZT, Lamivudine or Stavudine essentially causes the fatty degeneration of myocardium and NF-kBp65 activation in heart tissues while an analogous dosis of AZT, Lamivudine or Stavudine in a pharmaceutical composition with Meldonium or parallel use gives no statistically confident data of myocardium damage.

Further experiments were performed to make certain if applying parallel use of the Meldonium or AZT/Meldonium composition, Lamivudine/Meldonium pharmaceutical composition or Stavudine/Meldonium pharmaceutical composition have any advantage as compared with AZT, Stavudine, Lamivudine use in relation to NRTI neurotoxic effects. For this purpose in an experiment of analogous pattern, the experimental animals' neurological reactions were assessed after a fortnight. For this assessment, the common test of pain latent period in the tail compression model as well as the appraisal of cerebral cortex neuron degenerative transformation was made (molecular and external granule layers).

The experiments showed that AZT, Stavudine or Lamivudine provokes significant algesia and simultaneously causes a triple (3 fold) increase in degenerated neurons of the cerebral cortex as compared with the control. In the same time, the coadministration Meldonium with AZT, Lamivudine or Stavudine or use AZT/Meldonium, Lamivudine/Meldonium or Stavudine/Meldonium pharmaceutical compositions in comparison with an intact control caused no statistically significant increase of degenerated neuron number in the cerebral cortex what ascertains essential advantage of the claimed compositions as compared to the utilization of AZT, Stavudine or Lamivudine.

Thus, AZT/Meldonium, Lamivudine/Meldonium or Stavudine/Meldonium pharmaceutical compositions or coadministration of Meldonium AZT, Lamivudine or Stavudine used Meldonium positively differ from AZT, Stavudine or Lamivudine by that the claimed composition practically lacks essential toxic influence either on heart or cerebral tissues if doses containing AZT in quantity which per se cause essential damage of cardial and cerebral tissue are applied during 14 days. Therefore AZT/Meldonium, Lamivudine/Meldonium or Stavudine/Meldonium composition or coadministration of Meldonium with AZT, Lamivudine and Stavudine is characterized by a considerably higher degree of safety when clinically relevant doses of it are used.

Pharmaceutical compositions of Meldonium/AZT, Meldonium/Stavudine or Meldonium/Lamivudine may be formed for both oral and parenteral as well as topical administration.

For parenteral forms of introduction, Meldonium/AZT, Meldonium/Stavudine or Meldonium/Lamivudine composition is made either as a dry sterile powder for injections with or without a pharmaceutically suitable excipient or as solutions for injection/I.V. infusion. For injection solution forms, Meldonium and AZT, Meldonium/Stavudine or Meldonium/Lamivudine solutions in water, 0.9% NaCl, glucose aqueous solution of corresponding concentration or pharmaceutically appropriate buffer solutions compatible with both the actives. Meldonium concentration in injection dosage forms may be up to 40%, whereas the maximum concentration of AZT, Lamivudine or Stavudine depends on AZT, Lamivudine or Stavudine solubility in the corresponding solvent.

Oral administration forms (tablets with or without coating, capsules, caplets, dragees, pills, granules, powders or solutions) and the like of AZT/Meldonium, Meldonium/Stavudine or Meldonium/Lamivudine pharmaceutical compositions are made by use of common procedures of oral therapeutic form preparation, those pharmaceutically acceptable excipients (additives) being selected which are chemically compatible with AZT, Lamivudine or Stavudine and Meldonium. The quantity of AZT, Lamivudine or Stavudine in each oral introduction dose makes 5-500 mg, preferably 15 -40 mg or 100-300 mg, while the amount of Meldonium is from 5-4500 mg, most preferably 20-600 mg.

A possible pharmaceutical composition for oral use exemplifying but not exhausting the present invention is the following formulation of tablet production:

|  | Example 1 | Example 2 | Example 3 | Example 4 | Example 5 |
|---|---|---|---|---|---|
| AZT | 100 mg | 300 mg | 300 mg | 0 | 0 |
| Lamivudine | 0 | 0 | 0 | 100 mg | 150 mg |
| Meldonium | 250 mg | 600 mg | 60 mg | 200 mg | 300 mg |
| stearch | 20 mg | 40 mg | 20 mg | 20 mg | 25 mg |
| talc | 10 mg | 20 mg | 10 mg | 10 mg | 15 mg |
| Ca stearate | 1 mg | 2 mg | 1 mg | 1 mg | 1 mg |

|  | Example 6 | Example 7 | Example 8 | Example 9 | Example 10 |
|---|---|---|---|---|---|
| Lamivudine | 300 mg | 0 | 0 | 0 | 0 |
| Stavudine | 0 | 15 mg | 20 mg | 30 mg | 40 mg |
| Meldonium | 60 or 600 mg | 5 or 30 mg | 4 or 100 mg | 60 mg | 80 mg |
| stearch | 20 mg | 20 mg | 20 mg | 20 mg | 20 mg |
| talc | 10 mg | 10 mg | 10 mg | 10 mg | 10 mg |
| Ca stearate | 1 mg | 1 mg | 1 mg | 1 mg | 1 mg |

A possible pharmaceutical composition for oral use exemplifying but not exhausting the present invention is the following formulation of capsule manufacture:

|  | Example 11 | Example 12 | Example 13 | Example 14 | Example 15 |
|---|---|---|---|---|---|
| AZT | 100 mg | 0 | 0 | 0 | 0 |
| Lamivudine | 0 | 100 mg | 0 | 0 | 0 |
| Stavudine | 0 | 0 | 15 or 20 mg | 30 mg | 40 mg |
| Meldonium | 200 or 250 mg | 200 or 250 mg | 30 or 40 mg | 5, 15 or 60 mg | 20, 40 or 80 mg |
| aerosil | 5 mg | 5 mg | 5 mg | 5 mg | 5 mg |
| lactose | 66 mg | 66 mg | 66 mg | 66 mg | 66 mg |
| talc | 7 mg | 7 mg | 7 mg | 7 mg | 7 mg |
| Ca stearate | 3 mg | 3 mg | 3 mg | 3 mg | 3 mg |

A possible pharmaceutical composition for oral use exemplifying but not exhausting the present invention is the following formulation of solution or/and syrup manufacture:

|  | Example 16 | Example 17 | Example 18 |
|---|---|---|---|
| AZT | 10 mg/mL | 20 mg/mL | 50 mg/mL |
| Meldonium | 5 mg/mL or 20 mg/mL | 5 mg/mL or 40 mg/mL | 10 mg/mL or 100 mg/mL |
| Methyl-p-hydroxy-benzoate | 0.20-0.60 g | 0.20-0.60 g | 0.20-0.60 g |
| Propyl-p-hydroxy-benzoate | 0.01-0.1 g | 0.01-0.1 g | 0.01-0.1 g |
| Propylene glycol | 6.15-8.30 g | 6.15-8.30 g | 6.15-8.30 g |
| Sorbit | 120.00-150.50 g | 120.00-150.50 g | 120.00-150.50 g |
| Glycerine | 10.00-15.00 g | 10.00-15.00 g | 10.00-15.00 g |
| Purified water | 150 ml | 150 ml | 150 ml |

|  | Example 19 | Example 20 |
|---|---|---|
| Reverse Transcriptase Inhibitor | Lamivudine 10 mg/mL | Stavudine 1 mg/mL |
| Meldonium | 5 mg/mL or 20 mg/mL | 1 mg/mL or 5 mg/mL or 40 mg/mL |
| Methyl-p-hydroxybenzoate | 0.20-0.60 g | 0.20-0.60 g |
| Propyl-p-hydroxybenzoate | 0.01-0.1 g | 0.01-0.1 g |

-continued

| | | |
|---|---|---|
| Propylene glycol | 6.15-8.30 g | 6.15-8.30 g |
| Sorbit | 120.00-150.50 g | 120.00-150.50 g |
| Glycerine | 10.00-15.00 g | 10.00-15.00 g |
| Purified water | 150 ml | 150 ml |

INDUSTRIAL APPLICABILITY

Pharmaceutical compositions for treating retroviral infections which contain one of the reverse transcriptase inhibitors, viz., Zidovudine, Lamivudine, or Stavudine in clinically efficacious amount and Meldonium or its pharmacologically acceptable salt as well as pharmaceutically applicable excipients might be manufactured in a standard pharmaceutical plant.

The invention claimed is:

1. A pharmaceutical composition containing a clinically efficacious amount of nucleoside reverse transcriptase inhibitor and Meldonium or its pharmaceutically acceptable salt as well as pharmaceutically acceptable excipients.

2. A pharmaceutical composition according to claim 1 where the nucleoside reverse transcriptase inhibitor is selected from the group consisting of Zidovudine (AZT) (chemically: 3'-azido-3'-deoxythymidine), Lamivudine (chemically: (2R-cis)-4-amino-1-[2-(hydroxymethyl)-1,3-oxathiolan-5-yl]-2(1H)pyrimidinone) and Stavudine (chemically: 2',3'-didehydro-3'deoxythymidine).

3. A pharmaceutical composition according to claim 1 containing Meldonium and/or salt(s) thereof in such amount that the mass ratio of Meldonium/salt(s) to the nucleoside reverse transcriptase inhibitor is from 100:1 to 1:100, .

4. A pharmaceutical composition according to claim 3 distinguishing by the nucleoside reverse transcriptase inhibitor content of 1-500 mg and Meldonium and/or salt(s) thereof content of 5-2500 mg.

5. A pharmaceutical composition according to claim 4 distinguishing by Zidovudine content of 10-300 mg and Meldonium and/or salt(s) thereof and/or salt(s) thereof content of 5-600 mg.

6. A pharmaceutical composition according to claim 4 distinguishing by Lamivudine content of 10-300 mg and Meldonium and/or salt(s) thereof content of 5-600 mg.

7. A pharmaceutical composition according to claim 4 distinguishing by Stavudine content of 1-40 mg and Meldonium and/or salt(s) thereof content of 1-300 mg.

8. A pharmaceutical composition according to claim 1 distinguishing by its provision for oral or sublingual introduction and the form of an optionally coated tablet, capsule, caplet, dragee, pill, powder, or solution which contains 0.1-5.0 g actives according to weight in each dose of tablet, capsule, dragee, pill, or powder, or it is a 0.5~40% solution or syrup for oral administration.

9. A pharmaceutical composition according to claim 1 distinguishing by its provision for parenteral introduction and being a sterile powder which contains 0.1-5.0 g actives in each dose for parenteral introduction.

10. A pharmaceutical composition according to claim 1 distinguishing by its provision for parenteral introduction and being an injection solution which contains 1-200 mg/ml the nucleoside reverse transcriptase inhibitor and 1-400 mg/ml Meldonium and/or salt(s) thereof.

11. A pharmaceutical composition according to claim 10, wherein Meldonium and/or its salt is used in the form of a 0.9% NaCl solution.

12. A pharmaceutical composition according to claim 2 distinguishing by its provision for oral or sublingual introduction and the form of a tablet (with or without coating), capsule, caplet, dragee, pill, powder, or solution which contains 0.1-5.0 g actives according to weight in each dose of tablet, capsule, dragee, pill, or powder, or it is a 0.5~40% solution or syrup for oral administration.

13. A pharmaceutical composition according to claim 2 distinguishing by its provision for parenteral introduction and being a sterile powder which contains 0.1~5.0 g actives in each dose for parenteral introduction.

14. A pharmaceutical composition according to claim 2 distinguishing by its provision for parenteral introduction and being an injection solution which contains 1-200 mg/ml the nucleoside reverse transcriptase inhibitor and 1-400 mg/ml Meldonium and/or salt(s) thereof.

15. A pharmaceutical composition according to claim 3 containing Meldonium and/or salt(s) thereof in such amount that the mass ration of Meldonium/salt(s) to the nucleoside reverse transcriptase inhibitor is from 20:1 to 1:20.

16. A pharmaceutical composition according to claim 15 containing Meldonium and/or salt(s) thereof in such amount that the mass ratio of Meldonium/salt(s) to the nucleoside reverse transcriptase inhibitor is from 5:1 to 1:5.

17. A pharmaceutical composition according to claim 16 containing Meldonium and/or salt(s) thereof in such amount that the mass ratio of Meldonium/salt(s) to the nucleoside reverse transcriptase inhibitor is from 2:1 to 1:2.

* * * * *